United States Patent
Lark et al.

(10) Patent No.: US 12,369,924 B2
(45) Date of Patent: Jul. 29, 2025

(54) MEDICAL CUTTING DEVICES WITH COOLANT MODULES AND CHANNELS AND ASSOCIATED METHODS

(71) Applicant: Innovations 4 Surgery, LLC, Chapel Hill, NC (US)

(72) Inventors: Robert K. Lark, Chapel Hill, NC (US); Edward C. Skolnick, Denville, NJ (US); Antoine R. Kaeslin, Bethel, CT (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 365 days.

(21) Appl. No.: 18/087,741

(22) Filed: Dec. 22, 2022

(65) Prior Publication Data

US 2023/0190303 A1    Jun. 22, 2023

Related U.S. Application Data

(60) Provisional application No. 63/292,438, filed on Dec. 22, 2021.

(51) Int. Cl.
| | |
|---|---|
| *A61B 17/14* | (2006.01) |
| *A61B 17/32* | (2006.01) |
| *A61B 17/00* | (2006.01) |
| *A61B 17/56* | (2006.01) |

(52) U.S. Cl.
CPC ...... *A61B 17/142* (2016.11); *A61B 17/32002* (2013.01); *A61B 17/320068* (2013.01); *A61B 2017/00101* (2013.01); *A61B 2017/00115* (2013.01); *A61B 2017/00123* (2013.01); *A61B 2017/320075* (2017.08); *A61B 2017/564* (2013.01); *A61B 2217/007* (2013.01)

(58) Field of Classification Search
CPC ....... A61B 17/14; A61B 17/142; A61B 17/16; A61B 17/1644; A61B 17/32; A61B 17/320068; A61B 2017/1651; A61B 2017/320072; A61B 2017/320074; A61B 2017/320075; A61B 2017/320077; A61B 2017/320082; A61B 2017/320084; A61B 2017/320088
See application file for complete search history.

(56) References Cited

U.S. PATENT DOCUMENTS

| | | | |
|---|---|---|---|
| 3,786,814 A * | 1/1974 | Armao | A61B 18/02 604/113 |
| 4,008,720 A | 2/1977 | Brinckmann et al. | |
| 5,087,261 A * | 2/1992 | Ryd | A61B 17/144 606/177 |
| 5,122,142 A | 6/1992 | Pascaloff | |
| 5,188,102 A * | 2/1993 | Idemoto | A61M 3/0279 606/45 |
| 5,261,922 A | 11/1993 | Hood | |

(Continued)

*Primary Examiner* — Eric S Gibson
(74) *Attorney, Agent, or Firm* — Olive Law Group, PLLC

(57) ABSTRACT

Medical cutting devices with coolant modules and channels and associated methods are disclosed. According to an aspect, a cutting device includes a working blade body having a first end and a second end. The first end is configured to operatively connect to a source of movement. The second end defines a blade edge. The cutting device also includes a channel defined within the working blade body for carrying coolant for transferring heat from the second end of the working blade body.

19 Claims, 21 Drawing Sheets

(56) References Cited

U.S. PATENT DOCUMENTS

| | | | |
|---|---|---|---|
| 5,728,130 A | 3/1998 | Ishikawa | |
| 6,379,371 B1* | 4/2002 | Novak | A61B 17/320068 30/123.3 |
| 6,443,969 B1* | 9/2002 | Novak | A61B 17/320068 606/169 |
| 8,343,178 B2 | 1/2013 | Novak | |
| 8,348,880 B2 | 1/2013 | Messerly et al. | |
| D680,218 S | 4/2013 | Darian | |
| 9,320,528 B2* | 4/2016 | Voic | A61B 17/16 |
| 9,554,809 B2 | 1/2017 | Lark | |
| 10,238,415 B2 | 3/2019 | Naono | |
| 10,702,296 B2* | 7/2020 | Boudreaux | A61B 17/320068 |
| 11,471,168 B2* | 10/2022 | Lark | A61B 17/1628 |
| 2003/0204199 A1* | 10/2003 | Novak | A61B 17/320068 606/169 |
| 2005/0273127 A1* | 12/2005 | Novak | A61B 17/320068 606/169 |
| 2008/0009848 A1 | 1/2008 | Paraschiv | |
| 2013/0204285 A1 | 8/2013 | Gouery | |
| 2015/0005771 A1* | 1/2015 | Voic | A61B 17/14 606/79 |
| 2015/0088137 A1 | 3/2015 | Manna | |
| 2016/0089155 A1 | 3/2016 | Lark | |
| 2017/0056052 A1 | 3/2017 | Dickerson | |
| 2017/0340339 A1* | 11/2017 | Madan | A61B 17/320068 |
| 2017/0340344 A1* | 11/2017 | Boudreaux | A61B 17/1644 |
| 2017/0340345 A1* | 11/2017 | Yates | A61B 17/3211 |
| 2018/0344346 A1 | 12/2018 | Naono | |
| 2021/0121195 A1 | 4/2021 | Richards | |
| 2021/0186525 A1* | 6/2021 | Lark | A61B 17/1615 |
| 2022/0031425 A1* | 2/2022 | Gunacar | A61B 17/1673 |
| 2023/0190303 A1* | 6/2023 | Lark | A61B 17/16 606/82 |

\* cited by examiner

MEDICAL CUTTING DEVICES WITH COOLANT MODULES AND CHANNELS AND ASSOCIATED METHODS

CROSS REFERENCE TO RELATED APPLICATIONS

This application claims priority to U.S. Provisional Patent Application No. 63/292,438, filed Dec. 22, 2021, and titled MEDICAL DEVICES AND RELATED METHODS FOR TRANSFORMING BONE, OTHER TISSUE, OR MATERIAL, the content of which is incorporated herein by reference in its entirety.

This application is related to U.S. Nonprovisional patent application Ser. No. 18/087,715, filed Dec. 22, 2022, and titled MEDICAL CUTTING DEVICES WITH A STATIC CASING AND A BLADE WORKING BODY OF GREATER WIDTH AND RELATED METHODS.

This application is related to U.S. Nonprovisional patent application Ser. No. 18/087,727, filed Dec. 22, 2022, and titled MEDICAL CUTTING DEVICES WITH STATIC COMPONENTS HAVING TEMPERATURE SENSORS AND RELATED METHODS.

This application is related to U.S. Nonprovisional patent application Ser. No. 18/087,749, filed Dec. 22, 2022, and titled MEDICAL CUTTING DEVICES HAVING A BLADE WORKING BODY THAT DEFINES AN OPENING FOR EMITTING COOLANT THEREFROM AND RELATED METHODS.

This application is related to U.S. Nonprovisional patent application Ser. No. 18/087,766, filed Dec. 22, 2022, and titled MEDICAL CUTTING DEVICES HAVING A WORKING BLADE BODY WITH STATIC COMPONENTS AND RELATED METHODS OF USE.

TECHNICAL FIELD

The presently disclosed subject matter relates generally to medical devices. Particularly, the presently disclosed subject matter relates to medical cutting devices with coolant modules and channels and associated methods.

BACKGROUND

Traditional surgical saws, such as oscillating saws and reciprocating saws, allow users to cut bones (i.e. perform osteotomies) of relatively large diameters, such as the tibia and femur. These types of surgical saws, however, which are similar in many ways to the toothed saws used to cut wood, metal, and plastic, have significant disadvantages with respect to a patient's well-being. Because surgical saws utilize rapid motion of the saw blade to cut biological tissues, such as bone and cartilage, a significant amount of heat is generated along the blade and particularly at the blade and bone interface. This can be harmful to the patient since prolonged exposure of bone cells to temperatures at or in excess of 47° C. leads to necrosis of those osteocytes. Another disadvantage of these oscillating and reciprocating bone saws is that they produce uneven cuts, preventing ideal realignment and reduction of the osteotomy gap, which is detrimental to efficient healing of the bone. Oscillating bone saws, which utilize a number of sharpened teeth along their cutting edges, can tear neighboring soft tissues that are inadvertently caught in the serrations of the rapidly moving blade. Tearing of these soft tissues leads to significant blood loss and potential nerve damage, which undoubtedly hampers the health of the patient.

Traditional oscillating and reciprocating bone saws have employed a variety of different measures to address these disadvantages. With respect to the generation of excessive heat, these surgical saws can utilize irrigation systems to flush the surgical site near the blade and bone interface. These irrigation systems can be separate, requiring an additional device at the surgical site, or integrated. Although effective at flushing a surgical site of unwanted sources of added friction, these irrigation systems are relatively ineffective at actually cooling the blade at the blade and bone interface. For example, one design for a surgical saw that incorporates a means for irrigation comprises a channel between otherwise parallel portions of a saw blade through which fluid can flow out into the surgical site (See U.S. Pat. No. 5,087,261). This channel, though, can be easily compacted with surgical debris, rendering the integrated irrigation system unusable. In addition, providing a channel between parallel portions of the saw blade necessarily increases the likelihood of a wider, more uneven cut. Other designs for an oscillating bone saw include outlets along the blade's edge to facilitate irrigation along the blade and bone interface (See U.S. Pat. Nos. 4,008,720 and 5,122,142). However, these channels can be similarly compacted with surgical debris, rendering them useless. More so, channels along the very blade edge result in a blade edge that is not continuous, which reduces the cutting efficiency of the blade. Despite any potential efficacy in flushing a site of surgical debris, these systems do very little to actually cool the very blade edge, specifically at the blade and bone interface. Additionally, having copious amounts of irrigation fluid in the surgical site can hamper the surgeon's ability to visualize important anatomic structures.

Just as with saws used to cut wood, metal, and plastic, a user can avoid rough or uneven cuts by using a saw blade that incorporates more teeth along the edge of the blade and/or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut. Still, the improvement is not substantial enough to consider these measures a long-term solution with respect to producing smooth bone cuts. In fact, adding teeth or guiding the blade edge have little effect in preventing inadvertent tearing of neighboring soft tissues. Although efforts are taken to protect soft tissues from damage and prevent significant blood loss, the inherently close confines typical in performing any osteotomy make it extremely difficult to completely eliminate such damage, especially to those tissues that are unseen or positioned beneath the bone being cut. This is compounded by the fact that the saw blades used with many oscillating and reciprocating bone saws are relatively large.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the blade's edge by way of an ultrasonic horn. Being powered by sound waves, neighboring soft tissues are not damaged by these types of blades because the blade's edge effectively rebounds due to the elasticity of the soft tissue. Thus, the significant blood loss common with use of traditional bone saws is prevented. In addition, significantly more precise cuts are possible using ultrasonic bone cutting devices, in part, because the blade's edge does not require serrations.

Instead, a continuous and sharpened edge, similar to that of a typical scalpel, enables a user to better manipulate the surgical device without the deflection caused by serrations, which is common when using oscillating and reciprocating bone saws. Although ultrasonic cutting blades are advantageous in that they are less likely to tear neighboring soft tissues and more likely to produce relatively more even cuts, these types of blades still generate considerable amounts of heat.

As with traditional bone saws, separate or integrated irrigation systems are often utilized in order to flush the surgical site and generally provide some measure of cooling effect to the blade. However, many of these blades suffer from the same disadvantages as traditional bone saws that have tried to incorporate similar measures. For example, providing openings along the blade's edge through which fluid flows introduces voids in the cutting edge, thereby inhibiting the cutting efficiency of the blade (See U.S. Pat. No. 5,188,102). In addition, these fluid openings can be readily compacted with surgical debris, rendering them useless for their intended function. In other blade designs, the continuity of the blade is maintained and a fluid outlet is positioned just before the blade's edge (See U.S. Pat. No. 8,348,880). However, this fluid outlet merely irrigates the surgical site since it is positioned too far from the blade and bone interface to actually provide the necessary cooling effect. Also, it irrigates only one side of the blade. Another design for an ultrasonic cutting device, which claims to cool the blade, incorporates an irrigation output located centrally along the longitudinal axis of the blade (See U.S. Pat. No. 6,379,371). A recess in the center of the blade tip allows fluid to flow out of this output and toward the blade's edge, flow that is propelled by a source of pressure. However, the positioning of this irrigation output within the contour of the blade tip results in a bifurcation or splitting of the irrigation flow, such splitting tending to distribute fluid at an angle away from the blade's edge. Mentioned above, the excessive heat generated using any cutting blade, including an ultrasonic cutting blade, is focused most significantly at the blade and bone interface. This example for an ultrasonic blade with cooling capabilities, then, does little to actually cool the blade at the blade and bone interface, but instead serves merely to flush debris from the surgical site. Again, having copious amounts of irrigation fluid in the surgical site can hamper the surgeon's ability to visualize important anatomic structures. Furthermore, this ultrasonic blade is not well-suited to cutting large cross-sections of bone and is used almost exclusively in spine, oral or maxillofacial surgeries, which involve cutting of small bones.

Even assuming that any of the irrigation systems incorporated into the various bone saws provide some measure of cooling, thermal burning of both neighboring soft tissues and bone surfaces remains a significant problem. Because the working surface of the blade also moves rapidly, considerable heat is generated along its length, too. The dynamic motion of the surf contacts neighboring soft tissues, potentially burning them. With respect to an osteotomy, as the blade passes through the cross-section of bone, the freshly-cut bone surfaces remain in constant and direct contact with the rapidly vibrating shaft of the blade. As a result, it is not uncommon to burn the bone, produce smoke and, more importantly, kill osteocytes. In fact, simply lengthening an ultrasonic blade to accommodate large cross-sections of bone tissue, for example, increases the surface area through which heat can transfer and, thus, is avoided by manufacturers of these types of blades. While irrigation directed specifically toward the blade's leading edge may provide some measure of cooling at the blade and bone interface, irrigation alone is insufficient in trying to avoid prolonged exposure of bone tissue, for example, to temperatures in excess of 47° C. Therefore, there remains a need for a surgical device that is capable of cutting bones with large cross-sections, such as the femur, while maintaining a working temperature along the entirety of the blade shaft that does not inhibit proper healing of the bone tissue.

Furthermore, bone drilling has been shown to cause damage to bone beyond the necrotic layer closest to the cutting plane. Bone exposed to high cutting temperatures outside the necrotic layer has been shown to have reduced mechanical properties such as modulus, strength, and brittle behavior. The non-necrotic affected area can be larger than the necrotic layer itself. Bone not exposed to these high temperatures maintains its properties.

In some applications, there is a need to cool the functional end of the cutting device to prevent temperatures along the working surface of the blade or drill and the surrounding bone from reaching the limit for thermal necrosis of bone. This has been performed in the past using such techniques as saline spraying, which results in visualization issues at the cutting site, or slowing down the procedure itself to allow the blade to cool, which increases the operating room time. Thus, there is also a need to cool the blade while minimizing impact to current surgical procedures with regards to visibility and time of operation. Having a device that works to actively or passively cool blades just through internal (non-contact) methods would be a particularly useful solution because it would avoid the visualization challenge. Furthermore, something that cools the entire blade would be more useful than for example the use of coolant targeting a certain area like existing designs that use saline. All this serves in the context of reducing heat transfer to bone and therefore protecting the viability of the bone, which is crucial to allow for bone in-growth/osteointegration (e.g. cementless implant applications, union of bone interfaces, etc.).

There is also a unique opportunity to reinvent traditional bone cutting devices with the advent of 3D printing technologies, which provides the benefit of producing designs that were previously incompatible with traditional machining. For example, rocket engines are 3D printed at low cost and allow for complex cooling channels throughout the geometry of a given component. One could envision applying the same principles to the next generation of bone cutting devices.

For at least the aforementioned reasons, there is a need for improved surgical devices and techniques.

BRIEF DESCRIPTION OF THE DRAWINGS

Figure 1:
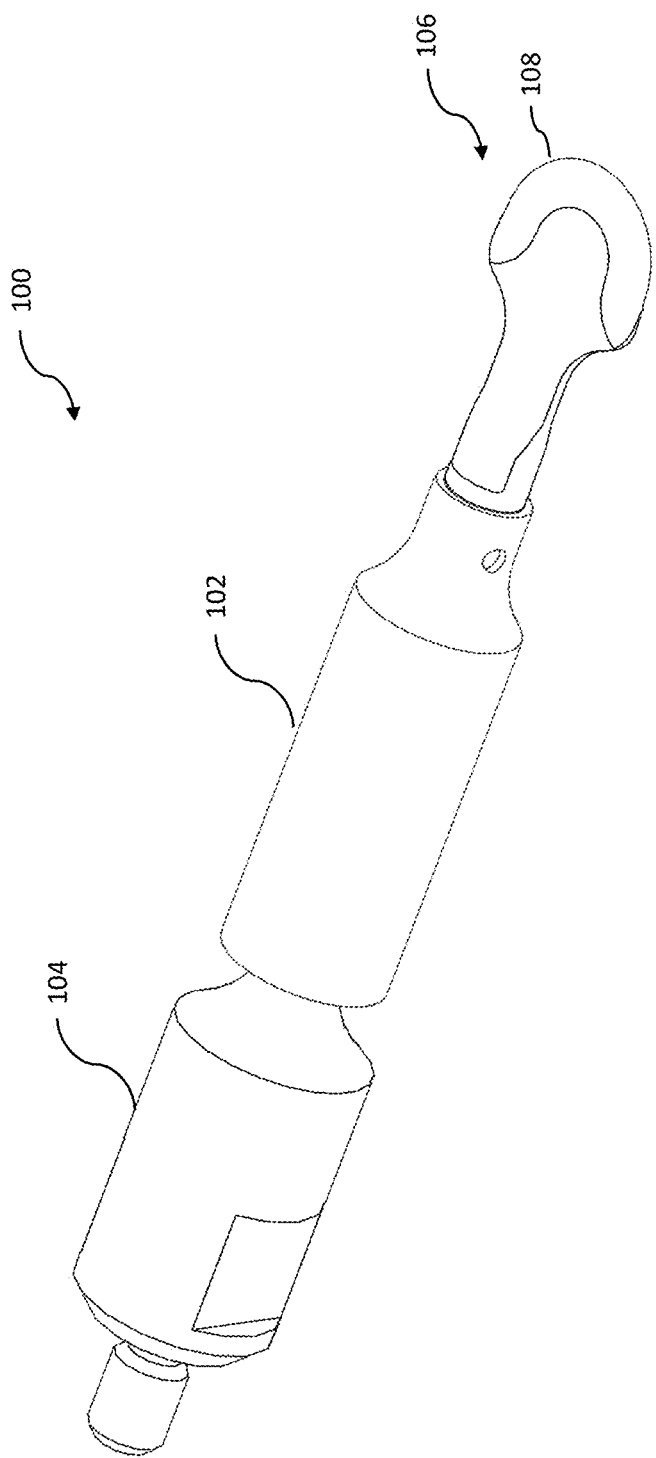
Figure 2:
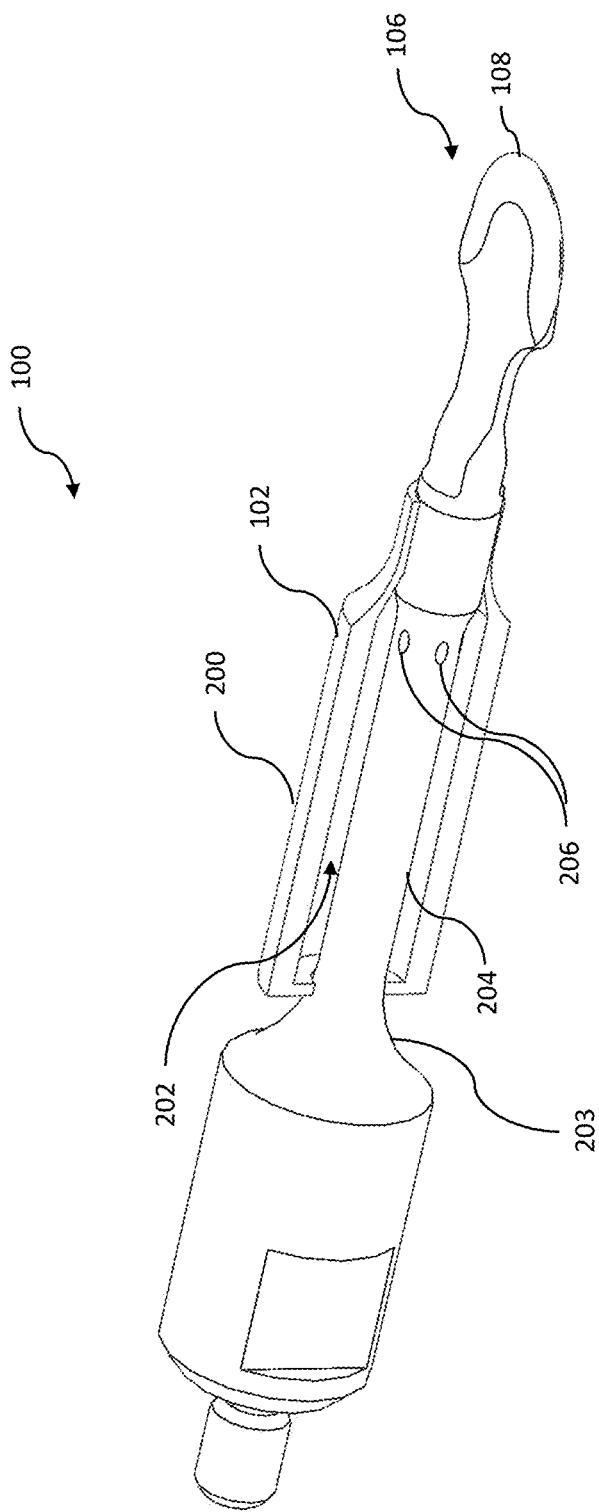
Figure 3:
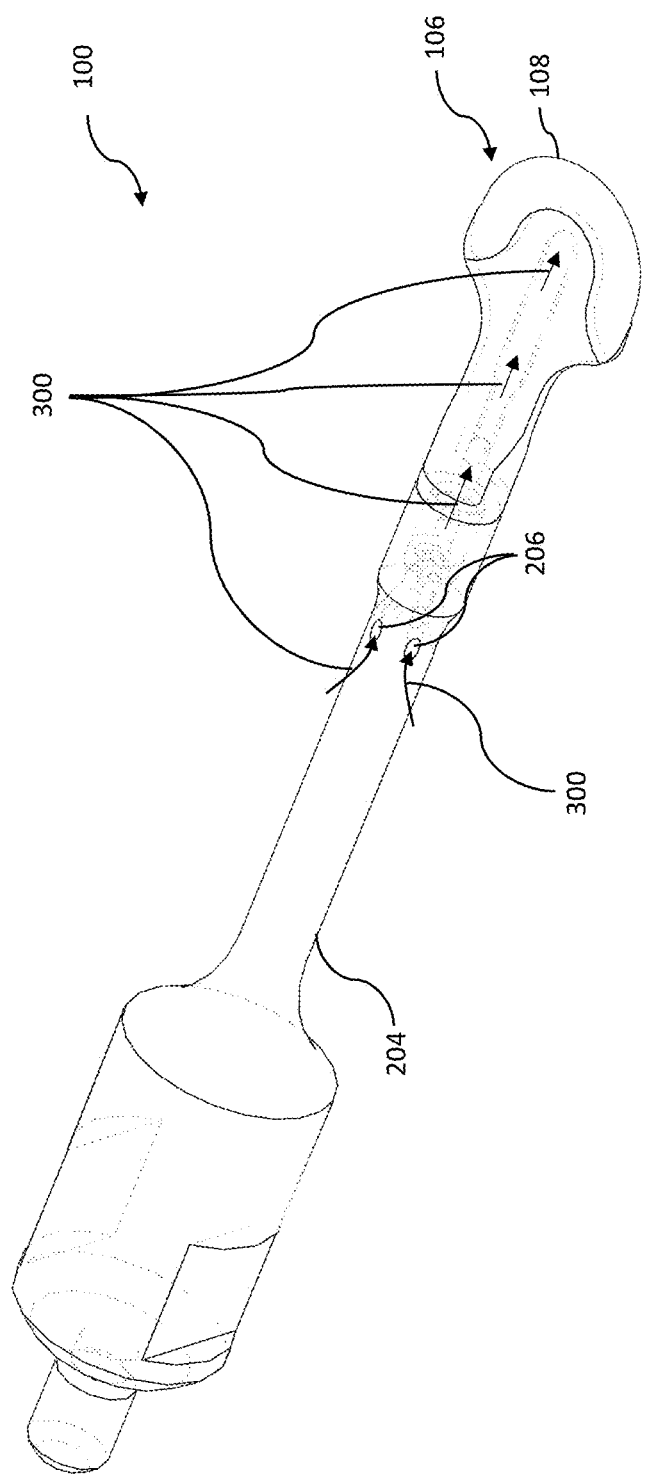
Figure 4:
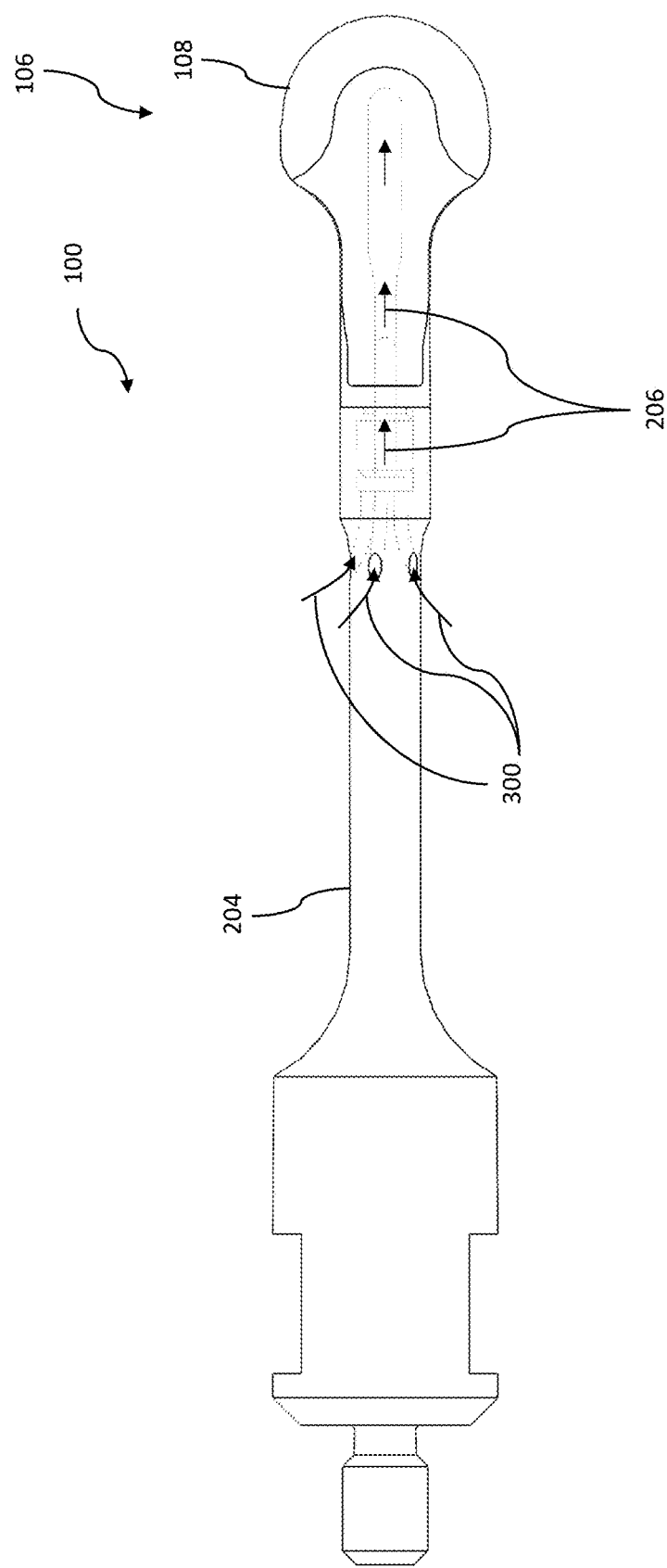
Figure 5:
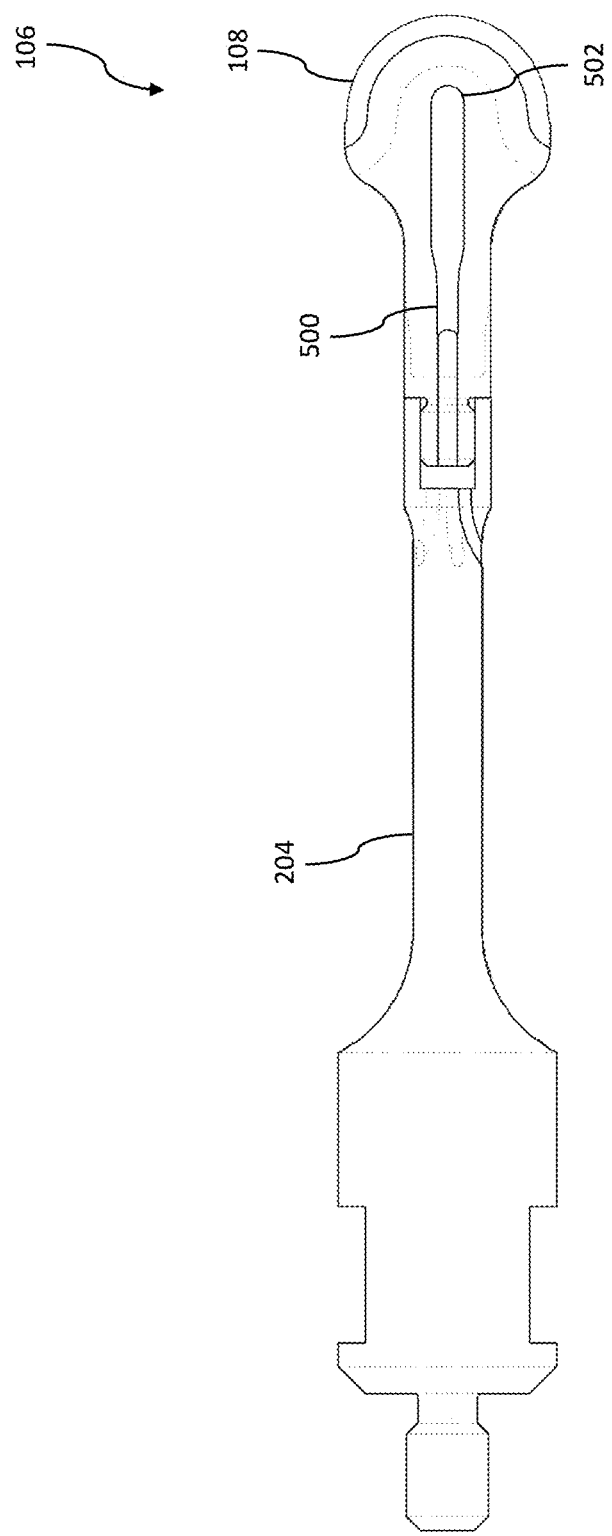
Figure 6:
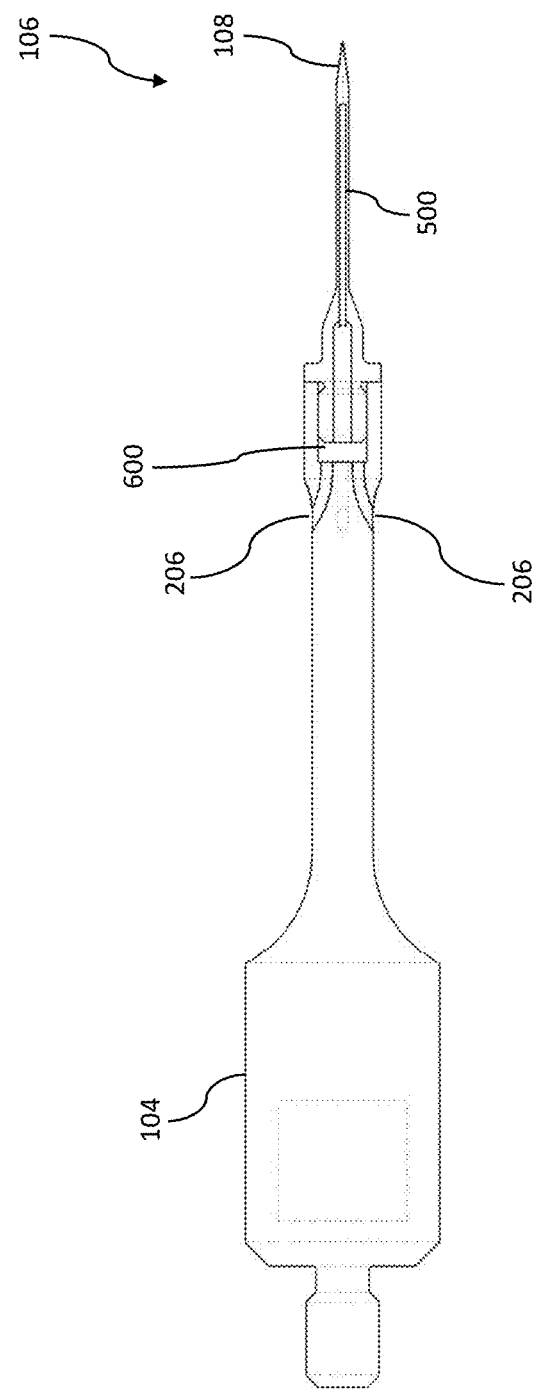
Figure 7:
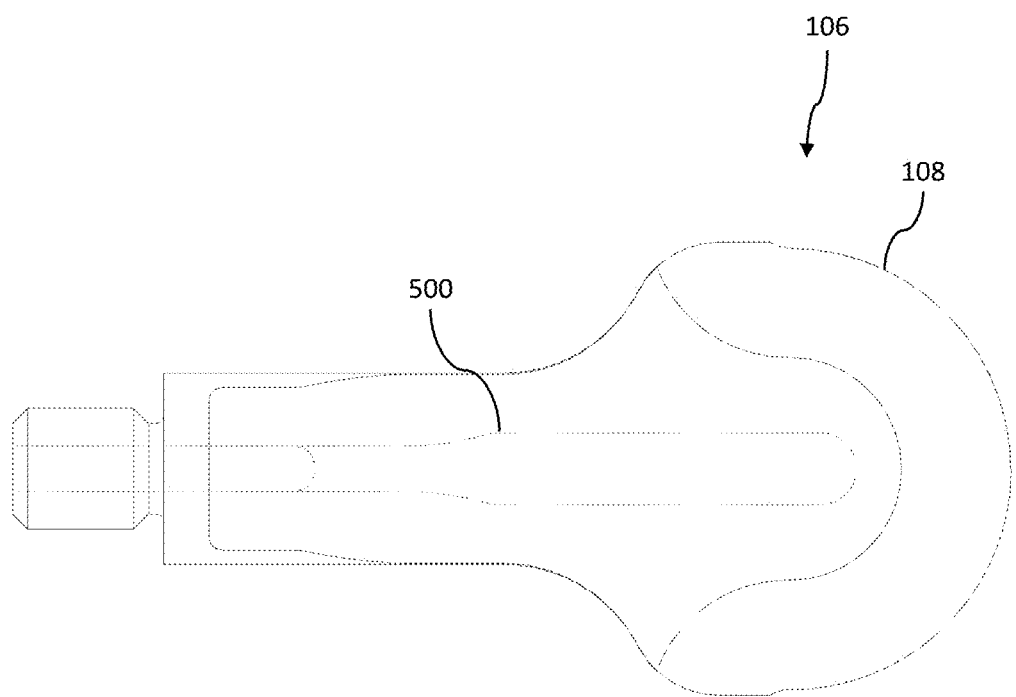
Figure 8:
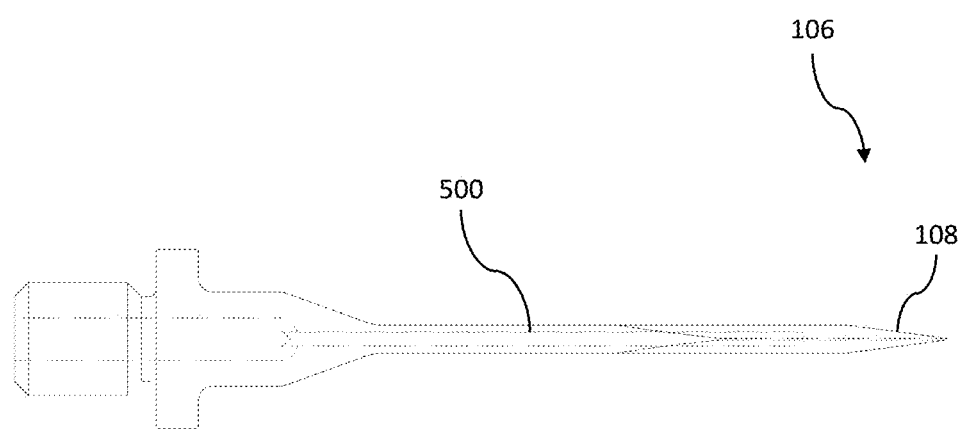
Figure 9:
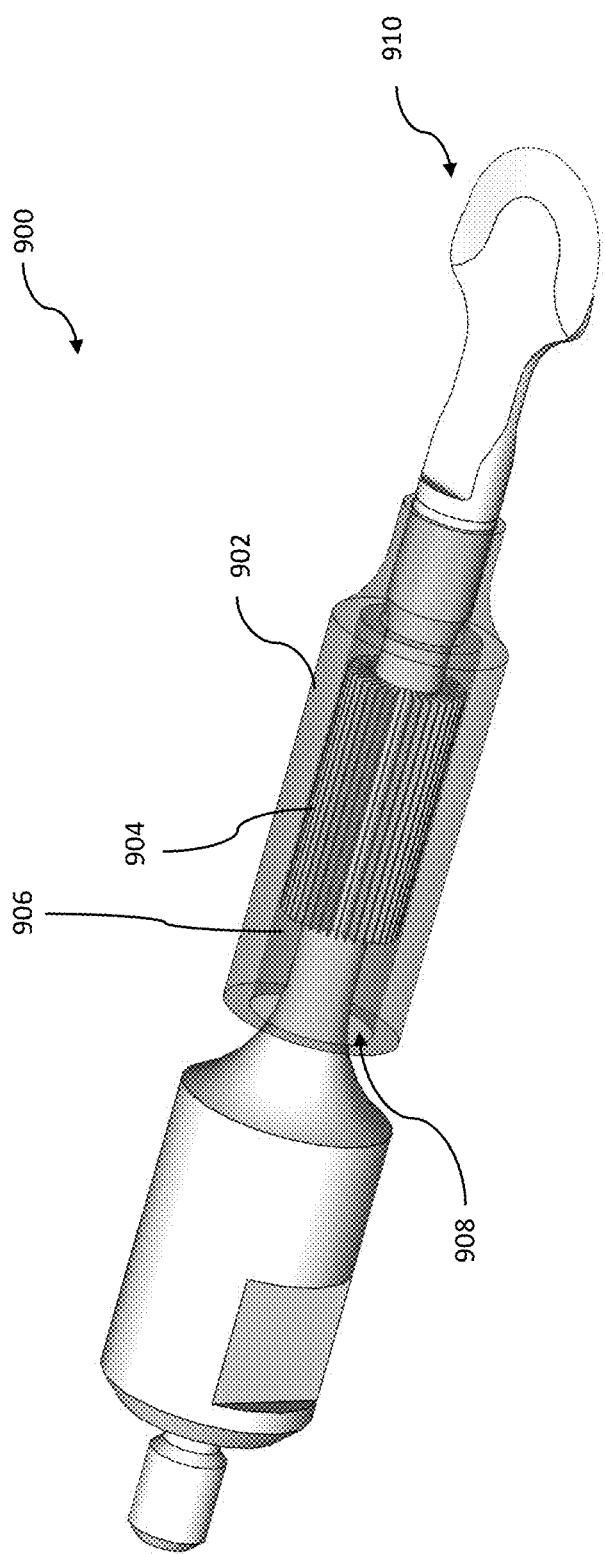
Figure 10:
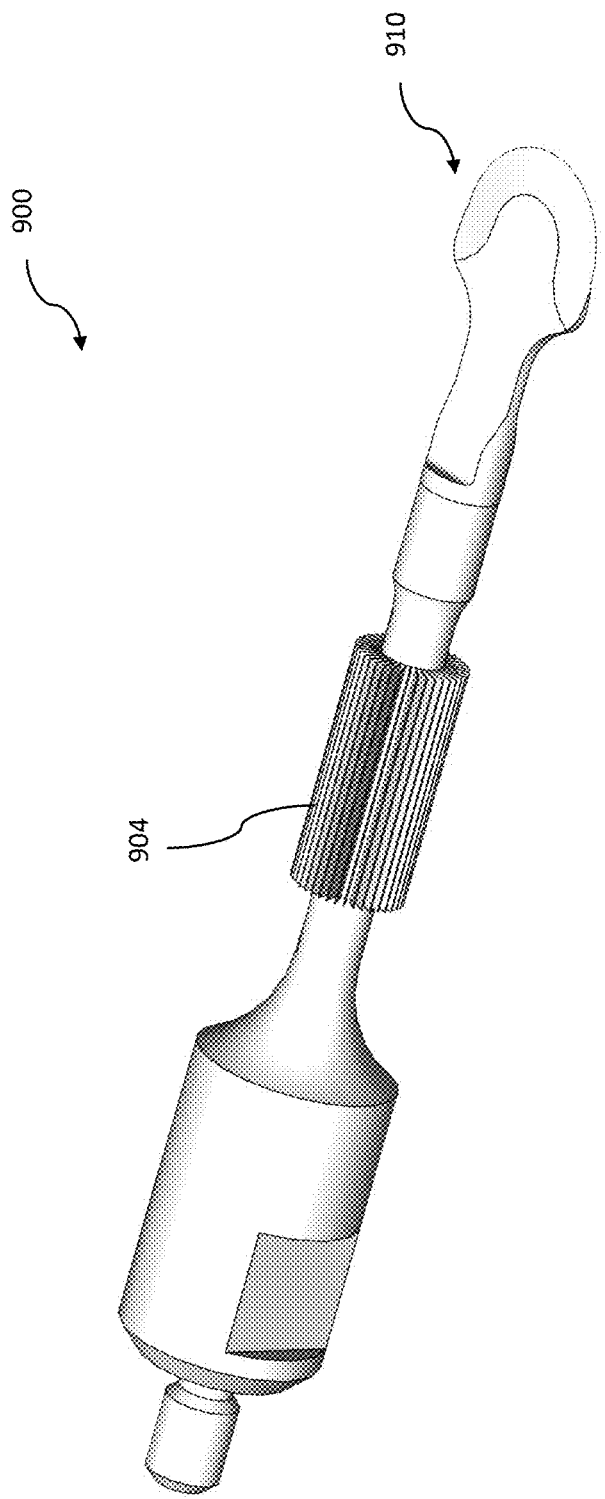
Figure 11:
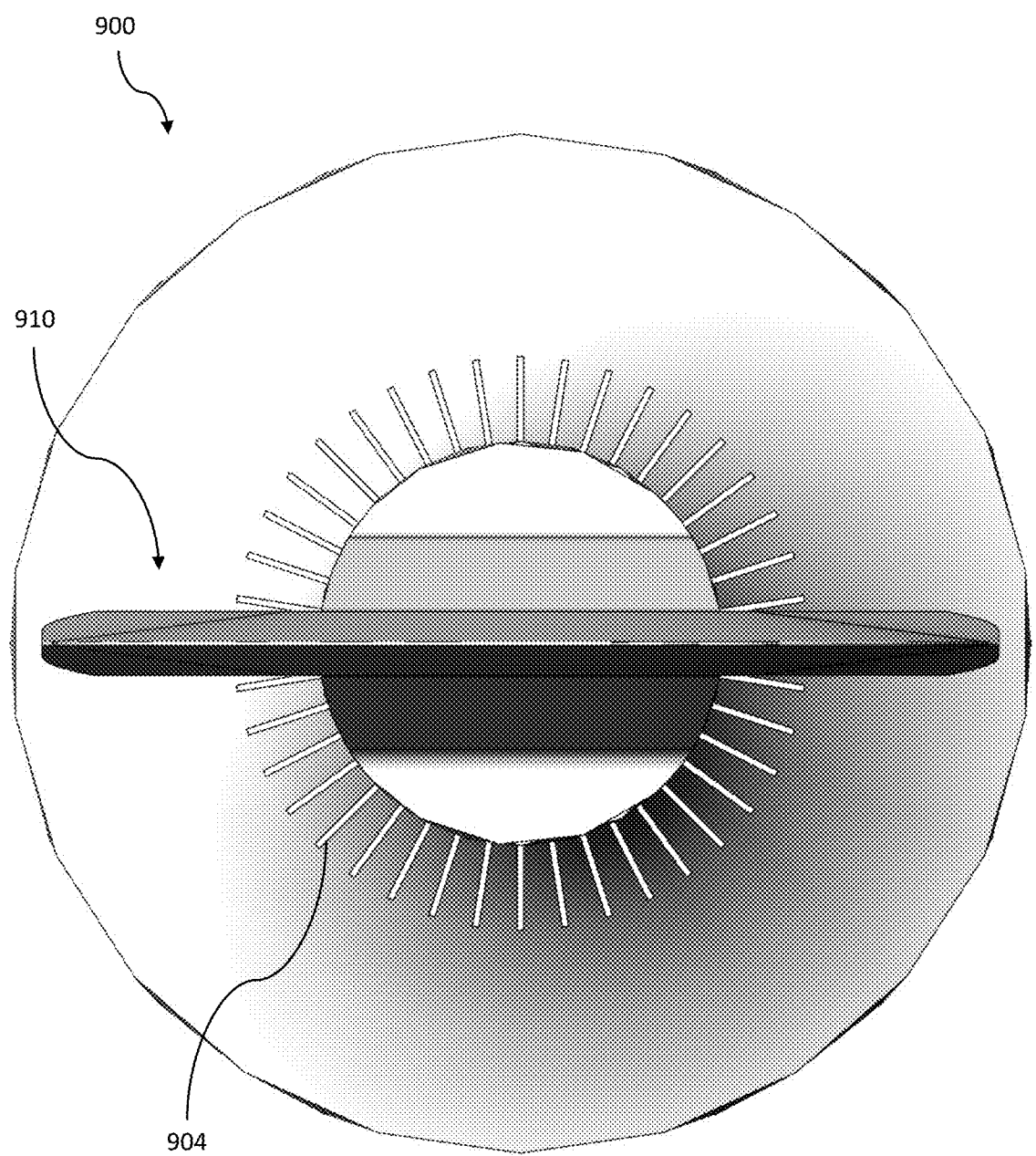
Figure 12:
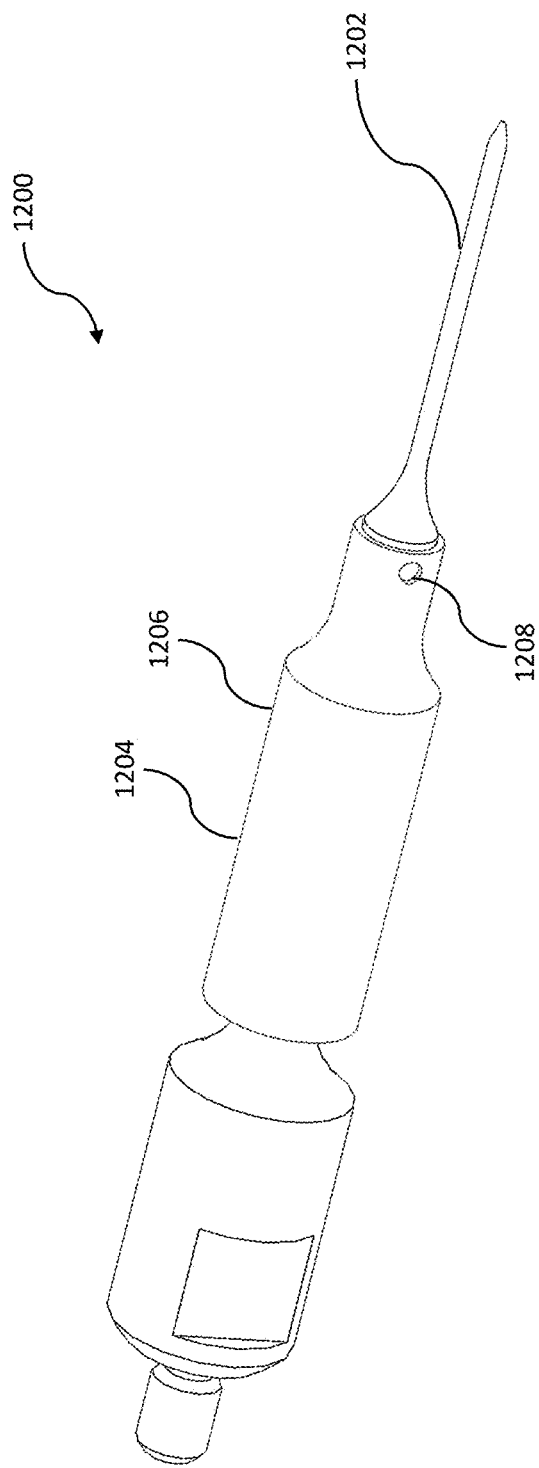
Figure 13:
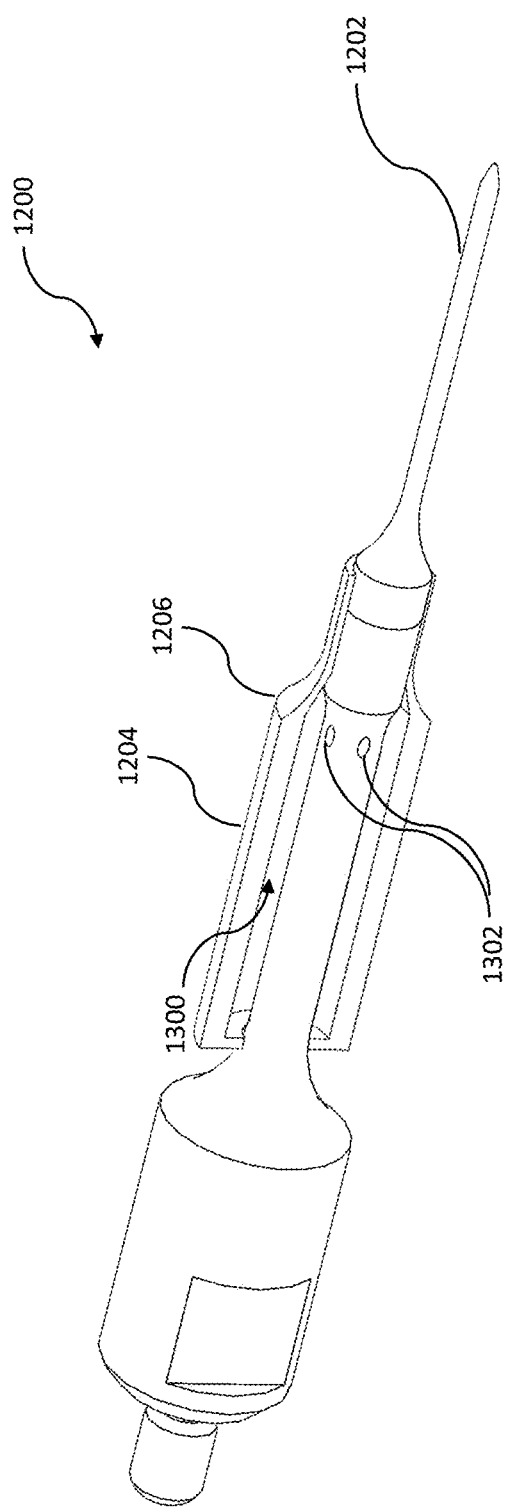
Figure 14:
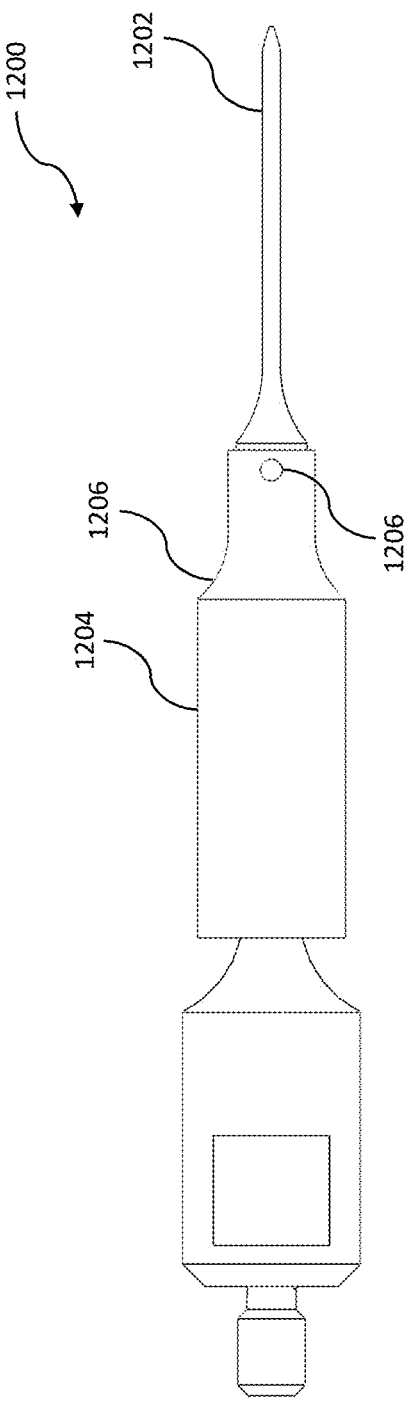
Figure 15:
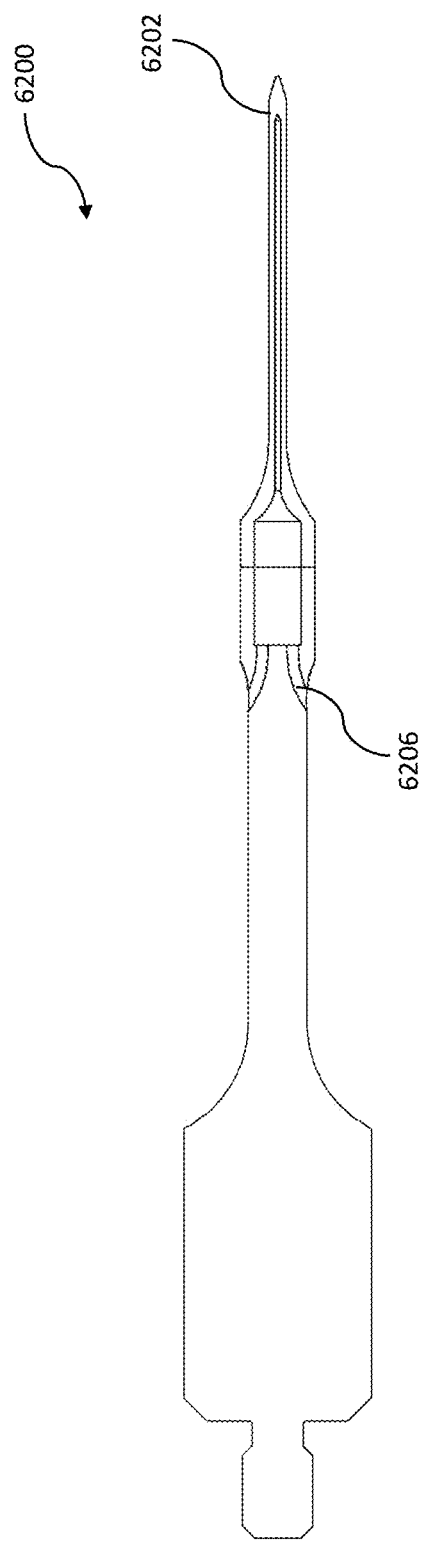
Figure 16:
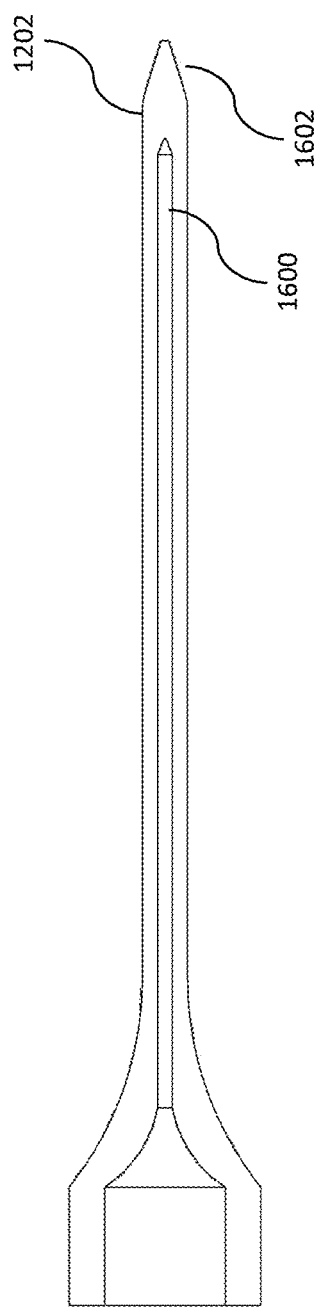
Figure 17:
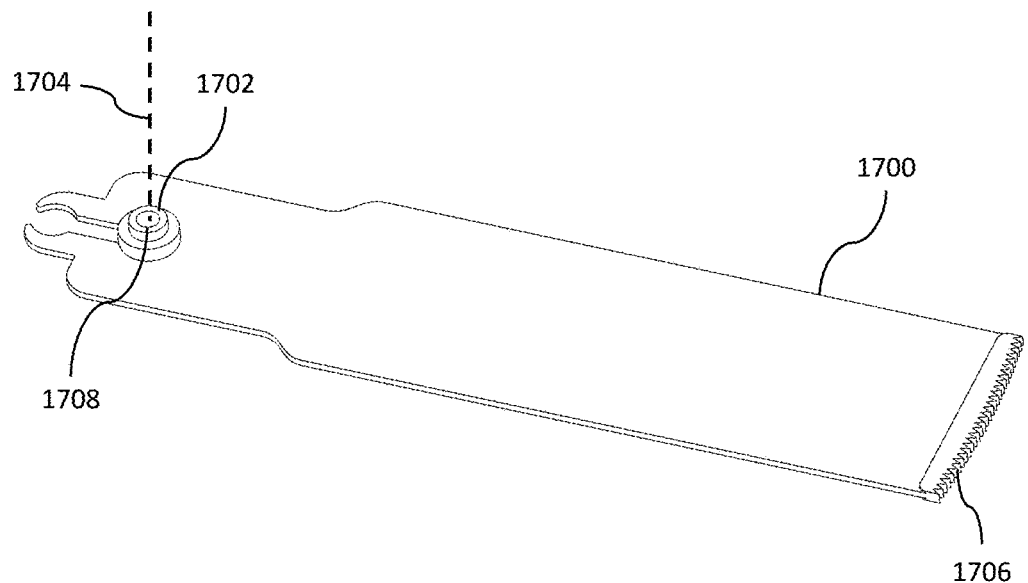
Figure 18:
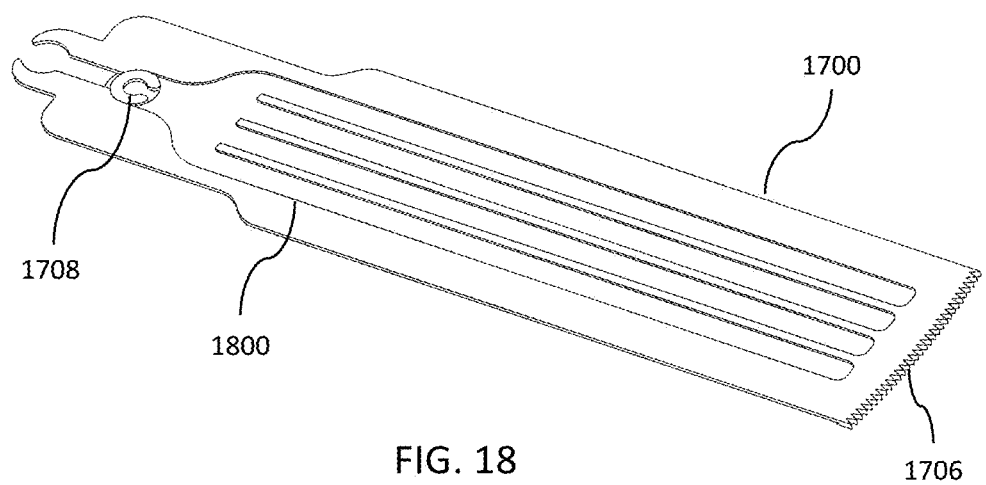
Figure 19:
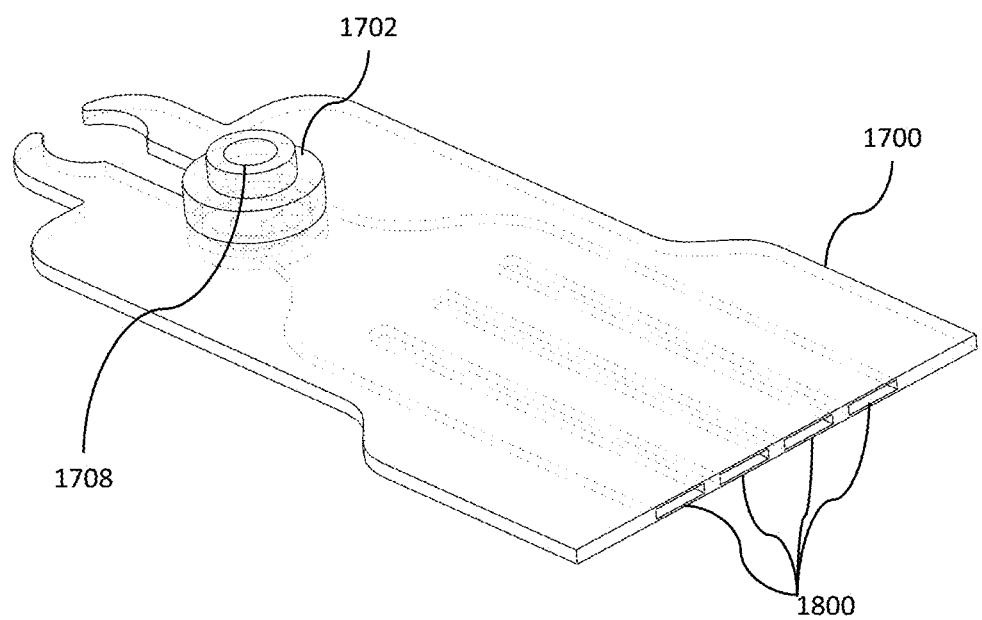
Figure 20:
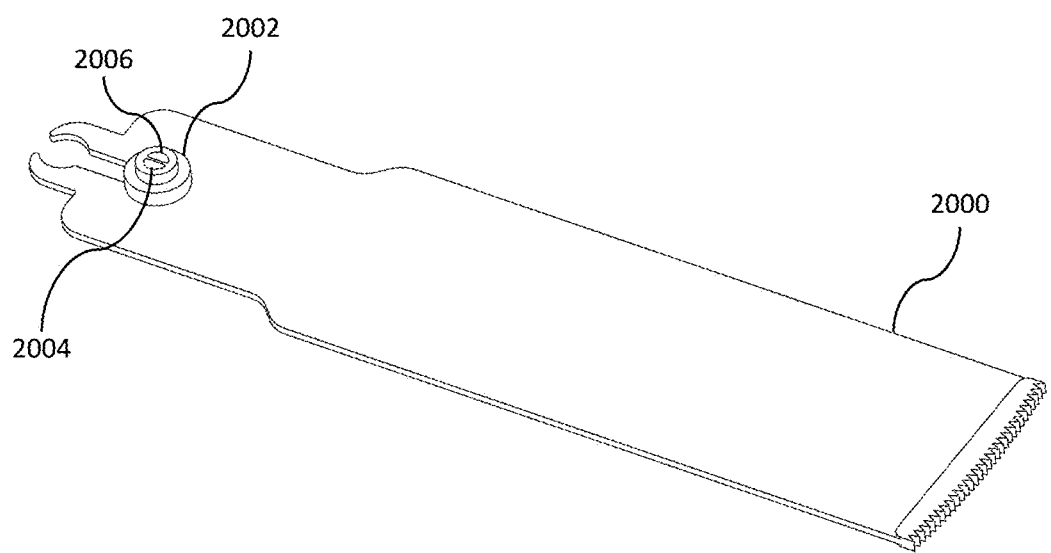
Figure 21:
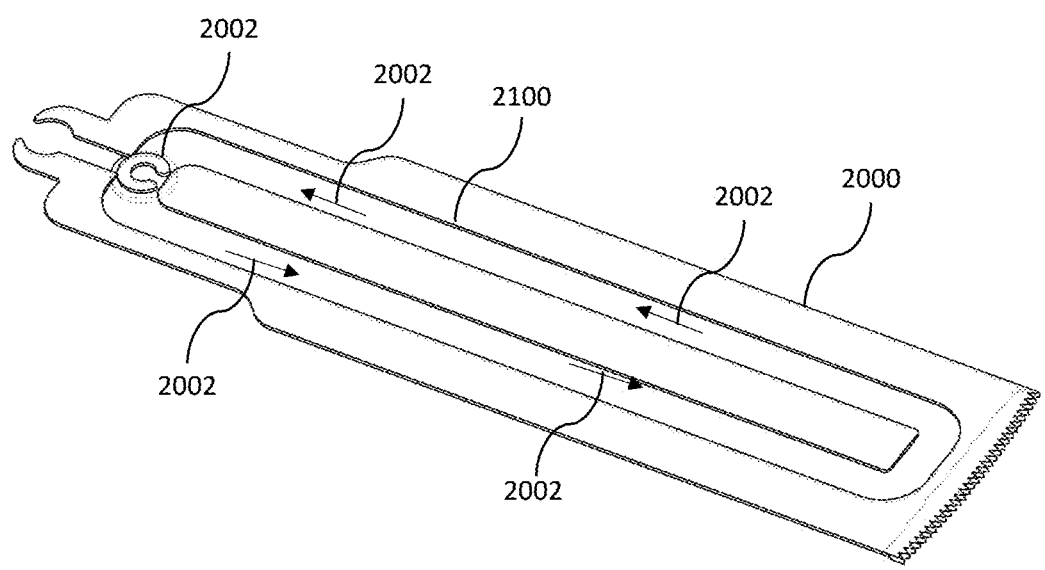
Figure 22:
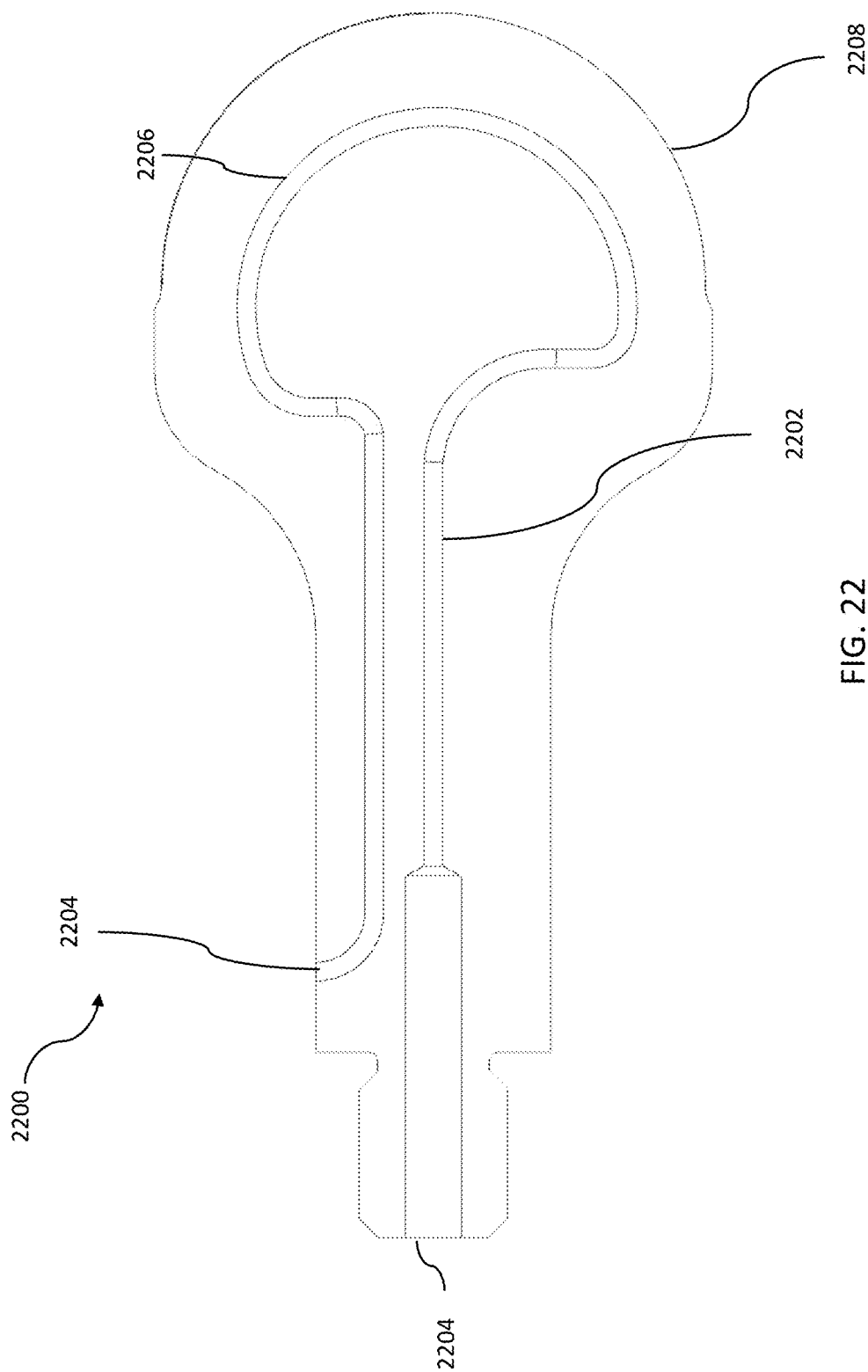
Figure 23:
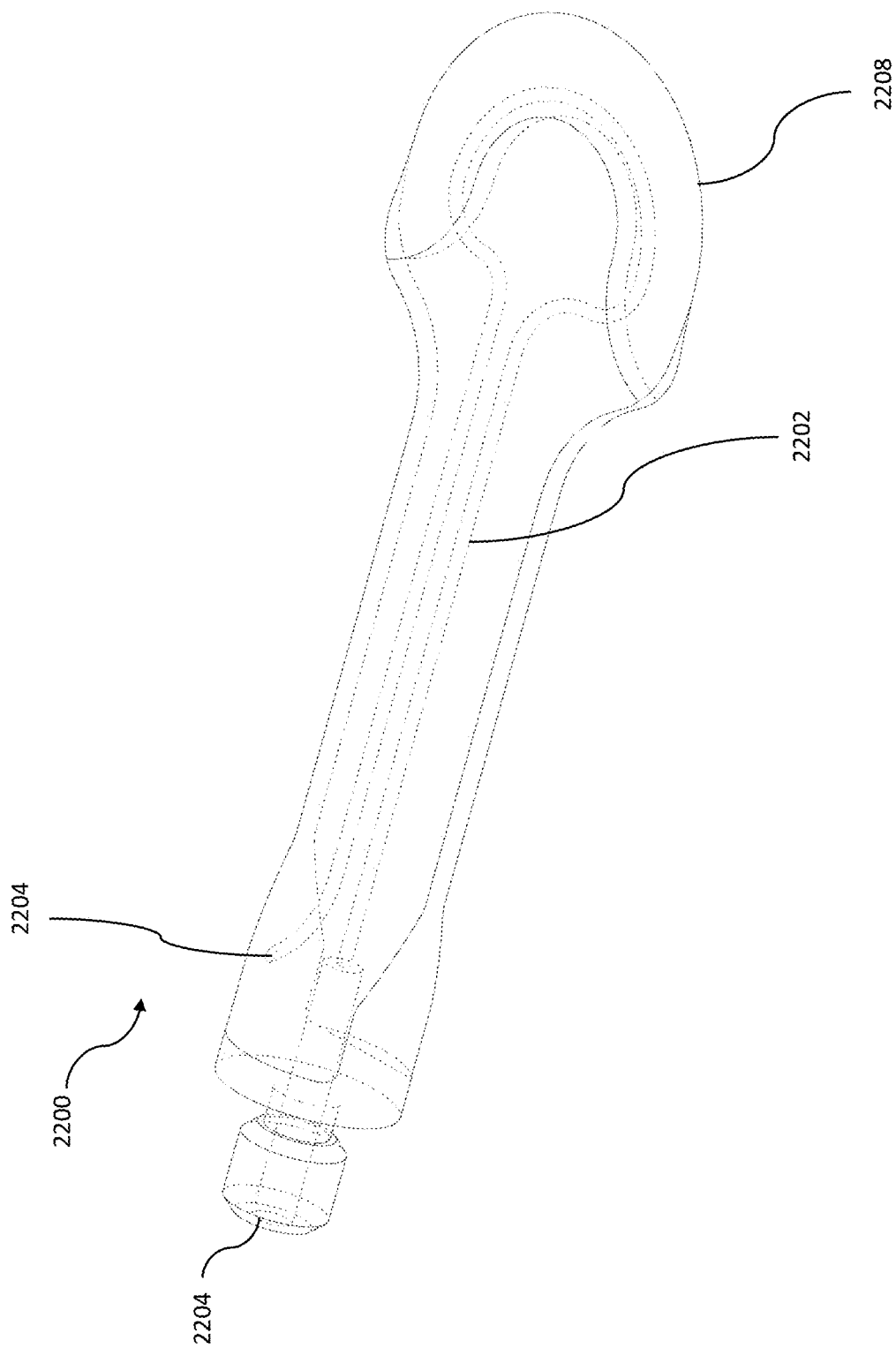

Having thus described the presently disclosed subject matter in general terms, reference will now be made to the accompanying Drawings, which are not necessarily drawn to scale, and wherein:

FIG. 1 is a top perspective view of a cutting device with a coolant module in accordance with embodiments of the present disclosure;

FIG. 2 is a perspective view of the cutting device shown in FIG. 1 with a housing of the coolant module in cut-away form such that internal components of the coolant module can be seen;

FIG. 3 is a perspective view of the cutting device shown in FIGS. 1 and 2 with the housing removed;

FIG. 4 is a top view of the cutting device shown in FIG. 3 with the housing removed for purpose of illustration;

FIG. 5 is a cross-sectional top view of the cutting device shown in FIGS. 1-4;

FIG. 6 is a side, cross-sectional view of the cutting device shown in FIGS. 1-5;

FIGS. 7 and 8 are a top view and a side view, respectively, of the cutting device shown in FIGS. 1-6;

FIG. 9 is a perspective top view of another example cutting device with a coolant module having cooling fins in accordance with embodiments of the present disclosure;

FIG. 10 is a top perspective view of the cutting device without the housing of the coolant module and the coolant;

FIG. 11 is a front view of the cutting device shown in FIGS. 9 and 10;

FIG. 12 is a perspective view of an example cutting device (without a handle being shown for ease of illustration) having a drill in accordance with embodiments of the present disclosure;

FIG. 13 is a perspective view of the cutting device shown in FIG. 12 with housing cut-away for showing its interior space;

FIG. 14 is a side view of the cutting device shown in FIG. 12;

FIG. 15 is a cross-sectional side view of the cutting device shown in FIG. 12;

FIG. 16 illustrates a cross-sectional side view of the cutting device shown in FIGS. 12-15;

FIG. 17 is a top perspective view of an example working blade body having a flexible coolant reservoir inlet in accordance with embodiments of the present disclosure;

FIG. 18 is a top perspective view of the working blade body of FIG. 17 with internal channels shown in broken lines;

FIG. 19 is a cross-sectional perspective view of the working blade body of FIGS. 17 and 18;

FIG. 20 is a top perspective view of an example working blade body having a flexible coolant reservoir inlet/outlet in accordance with embodiments of the present disclosure;

FIG. 21 is a top perspective view of the working blade body of FIG. 20 with an internal channel shown in broken lines;

FIG. 22 is a top view of an example working blade body having a looping channel for cooling in accordance with embodiments of the present disclosure; and FIG. 23 is a top perspective view of the working blade body shown in FIG. 22.

SUMMARY

The presently disclosed subject matter relates to medical cutting devices with coolant modules and channels and associated methods. According to an aspect, a cutting device includes a working blade body having a first end and a second end. The first end is configured to operatively connect to a source of movement. The second end defines a blade edge. The cutting device also includes a channel defined within the working blade body for carrying coolant for transferring heat from the second end of the working blade body.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As referred to herein, the term "cutting device" can be any suitable component movable for cutting into or generally transforming a material (e.g., bone). The cutting device can include a blade that operates through large or small (e.g., vibrations) mechanical motion. The motion can be in a specific direction(s). For example, the cutting device can be moved in an oscillating manner, flexing, bending, rotating, torsionally, longitudinally, and the like.

FIG. 1 illustrates a top perspective view of a cutting device 100 with a coolant module 102 in accordance with embodiments of the present disclosure. Referring to FIG. 1, the cutting device 100 is shown without a handle and housing for simplicity of illustration. It is noted that the handle and housing may be similar to the handle and housing of the cutting device of FIG. 1 or any other suitable handle and housing.

With continuing reference to FIG. 1, the cutting device 100 may include an end 104 for connection to the housing. Further, the cutting device 100 may include a cutting end, generally designated 106, with an arced or curved blade 108 for cutting bone or other material as described by example herein. For example, an appropriately-connected piezoelectric transducer can generate and propagate ultrasonic vibrations to the cutting end 106.

The coolant module 102 functions to be a heat sink for the heat generated by operation of the cutting device 100. Particularly, during operation the cutting by cutting end 106 can cause a significant amount of heat to be generated. This heat can be transferred along the cutting end 106 to the coolant module 102 where it is substantially dissipated, thus significantly reducing the heat at the cutting end 106. As a result, less heat is adversely applied to bone or other biological material at the point of cutting. One or more of the components of the cutting end 106 may be made of good conductors of heat.

Now turning to FIG. 2, this figure illustrates a perspective view of the cutting device 100 shown in FIG. 1 with a housing 200 of the coolant module 102 in cut-away form such that internal components of the coolant module 102 can be seen. The housing 200 defines an interior space 202 for holding the internal components. Particularly, a main body 203 of the cutting device 200 can include a structural component 204 that extends along an axis of the housing 200 for attaching the cutting end 106 to the handle and the housing. In this example, the remainder of the volume in the interior space 202 is filled with a coolant. Examples of coolant includes, but is not limited to, gases such as CO2, liquid nitrogen, cooled water, or any other suitable cooling fluids or material. Thus, the housing 200 functions as a coolant reservoir. Within the structural component 204 are defined several channels (not shown) that lead near the cutting end 106. Openings 206 defined at ends of the channels such that the coolant contained in the interior space 202 can reach the cutting end to thereby cool the cutting end 106 when it becomes heated during operation. The channels may connect internally near the cutting end 106 or elsewhere between the openings 206 and the cutting end 106 such that the coolant may access the full extent of the blade for the purposes of cooling. The coolant module can store and provide a source of coolant to the channels.

It is noted that the cutting end 106 may be releasably attachable to the body 203 by a suitable mechanism. Further, it is noted that the channel(s) fluidly connected to openings 206 may extend to meet and fluidly connect to an associated set of channel(s) within the cutting end 106. As a result, the 2 separate components of the body 203 and the cutting end 106 may transfer or move fluid from within the coolant module 102 to the cutting end for removing heat or transferring thermal energy from the cutting end 106.

For purpose of illustration, FIG. 3 illustrates a perspective view of the cutting device 100 shown in FIGS. 1 and 2 with the housing 200 removed. Arrows 300 depict a direction of flow of coolant from the interior space (indicated by reference numeral 202 in FIG. 2) through openings 206, and to cutting end 106. FIG. 4 illustrates a top view of the cutting device shown in FIG. 3 with the housing 200 removed for purpose of illustration.

FIG. 5 illustrates a cross-sectional top view of the cutting device 100 shown in FIGS. 1-4. Referring to FIG. 5, this figure shows an internal channel 500 that extends to multiple channels that connect to openings (e.g., openings 206 in FIG. 2) at one end. Thus, coolant from the interior space (space 202 in FIG. 2) can pass into the cutting end 106. The channel 500 extends into the cutting end 106 at a farthest extent to end 502. At end 502, heat generated within cutting end 106 can transfer to coolant within end 502. Coolant within end 502 can transfer through the channel 500 into coolant within the interior space (space 202 shown in FIG. 2).

FIG. 6 illustrates a side, cross-sectional view of the cutting device 100 shown in FIGS. 1-5. Referring to FIG. 6, the figure shows multiple openings 206 being fluidly connected to channel 500 via multiple channels 600.

FIGS. 7 and 8 illustrate a top view and a side view of the cutting device 100 shown in FIGS. 1-6. Referring to FIGS. 7 and 8, channel 500 is shown with broken lines as it is an interior feature.

FIG. 9 illustrates a perspective top view of another example cutting device 900 with a coolant module 902 having cooling fins 904 in accordance with embodiments of the present disclosure. Referring to FIG. 9, the cutting device 900 is shown without a handle and housing for simplicity of illustration. It is noted that the handle and housing may be similar to the handle and housing of the cutting device of FIG. 1 or any other suitable handle and housing. The coolant module 902 includes the cooling fins 902 and a coolant 906 positioned within an interior space 908 defined within the coolant module 902. The coolant module 902 can be configured to seal the interior for holding the coolant 906 to act as a reservoir. The cooling fins 902 are operatively connected to a cutting end 910 for receipt of transferred heat. In this example, there are multiple cooling fins along an axis of the device, but they may be in any suitable arrangement. Further, in this example, the cooling fins 904 are surrounded by coolant 906 such that the heat at the cooling fins 904 can be transferred to the coolant 904. A housing of the coolant module 902 surrounds the coolant 906 such that the heat can be transferred from the coolant 906 through the housing of the coolant module 902 and to the outside environment. Example coolant includes, but is not limited to, gases such as $CO_2$, liquid nitrogen, cooled water, or any other suitable cooling fluids or material.

FIG. 10 illustrates a top perspective view of the cutting device 900 without the housing of the coolant module 902 and the coolant 906. FIG. 11 illustrates a front view of the cutting device 900 shown in FIGS. 9 and 10.

FIG. 12 illustrates a perspective view of an example cutting device 1200 (without a handle being shown for ease of illustration) having a drill 1202 in accordance with embodiments of the present disclosure. The cutting device 1200 includes a coolant module 1204. It is noted that this may be an ultrasonic application or any other suitable application. In this example, the drill 1202 is an ultrasonic drill for drilling into or otherwise cutting into bone or other material. The drill 1202 can be suitably rotated at high speed by an ultrasonic mechanism (e.g., torsionally rotated back and forth at a high operating frequency). Alternative to a drill, this component may be any suitable type providing rotary or torsional motion. The coolant module 1204 includes a housing 1206, which may store cooling fins, coolant, or other components for cooling in accordance with embodiments of the present disclosure.

The cutting device 1200 includes a temperature sensor 1208 configured to detect a temperature in accordance with embodiments of the present disclosure. The temperature 1208 may be operatively connected to electronic circuitry for providing feedback about detected temperature in accordance with embodiments of the present disclosure.

FIG. 13 illustrates a perspective view of the cutting device 1200 shown in FIG. 12 with housing 1206 cut-away for showing its interior space. Referring to FIG. 13, the housing 1206 defines an interior space 1300 for containing a coolant along with openings 1302 similar to the openings 206 and other aspects of the coolant module 102 shown in FIG. 2. Similar to the cutting device 100 of FIG. 2, internal pathways can merge to a main channel that extends to the drill 1202 or near to the drill 1202 for cooling the drill 1202. Alternatively, the internal pathways can separately extend to the drill 1202 or near the drill. FIG. 14 is a side view and FIG. 15 is a cross-sectional side view of the cutting device 1200.

FIG. 16 illustrates a cross-sectional side view of the cutting device 1200 shown in FIGS. 12-15. Referring to FIG. 16, a main internal channel 1600 is defined in the interior and extends near a tip 1602 of the cutting device 1200.

FIG. 17 illustrates a top perspective view of an example working blade body 1700 having a flexible coolant reservoir inlet 1702 in accordance with embodiments of the present disclosure. Referring to FIG. 17, the coolant reservoir inlet 1702 is located at a center of an axis 1704 of rotation of the working blade body 1700. This is the axis 1704 upon which the working blade body is rotated for cutting with blade end 1706. The inlet 1702 defines an opening 1708 through which coolant may be provided for flow into one or more channels within the working blade body 1700. For example, FIG. 18 is a top perspective view of the working blade body 1700 of FIG. 17 with internal channels 1802 shown in broken lines.

FIG. 19 is a cross-sectional perspective view of the working blade body 1700 of FIGS. 17 and 18. Referring to FIG. 19, a cross section of the internal channels 1802 can be seen.

FIG. 20 illustrates a top perspective view of an example working blade body 2000 having a flexible coolant reservoir inlet/outlet 2002 in accordance with embodiments of the present disclosure. Referring to FIG. 20, the coolant reservoir inlet/outlet 2002 is located at a center of an axis of rotation of the working blade body 2000 similar to the working blade body 1700 of FIGS. 17-19. The inlet/outlet 2002 defines an inlet opening 2004 through which coolant may be provided for flow into one or more channels within the working blade body 2000. The inlet/outlet 2002 also defines an outlet opening 2006 from which coolant may exit. For example, FIG. 21 is a top perspective view of the working blade body 2000 of FIG. 20 with an internal channel 2100 shown in broken lines. Referring to FIG. 21, a direction of flow of coolant is indicated by arrows 2102.

FIG. 22 illustrates a top view of an example working blade body 2200 having a looping channel 2202 (shown as broken lines as interior components) for cooling in accordance with embodiments of the present disclosure. Referring to FIG. 22, the working blade body 2200 defines openings 2204 for entry and exit of coolant in the channel 2202. The channel 2202 has a curved portion 2206 that coincides with a curved blade edge 2208.

FIG. 23 illustrates a top perspective view of the working blade body 2200 shown in FIG. 22. Referring to FIG. 23, the looping channel 2202 is shown in broken lines again since it is an interior component.

It is noted that embodiments of the present disclosure are described as producing or having ultrasonic movement produced by a piezoelectric transducer or any other suitable source for motion. It is noted that in the alternative the movement may be any suitable type of movement produced by any suitable source (e.g., large/macro based motions similar to more traditional bone cutting devices). Further, cutting may be applied to any suitable material or technical field. Suitable mechanical sources could include anything from piezoceramics, electro-mechanical motors, user generated hand motion, etc. However, its important to note that all types of mechanisms can produce equivalent types of movements. These could include, but are not limited to, axial motion, bending motion, torsional motion, flexural motion, etc. It is also feasible that the source of mechanical motion can combine all of these modes of motion to create more complex movements. Regardless of the motion and/or the manner in which it is produced, there would be a resultant motion at the end of the functional device/blade edge. This motion would, under the claims of this patent, be captured within the bounds of the static casing/rails which function to share load, decouple motion, and prevent heat transfer to the functional working surfaces. Examples include oscillating/sagittal/reciprocating medical bone cutting saws, medical rotary drills, medical rotary burs, construction hammer drills, construction rotary hammer, wood cutting axes, construction oscillating multi-tools, oscillating medical cast saws, cutting saws, etc. The principles of the claims presented in this patent could be applied to all of these devices with equivalently realized benefits.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A cutting device comprising:
a working blade body including a first end and a second end, the first end being configured to operatively connect to a source of movement;
a plurality of channels defined within the working blade body for carrying coolant within the working blade body for transferring heat from the second end of the working blade body; and
a coolant module is attached to a main body and defines an interior space for storing the coolant, wherein a portion of the main body extends through the interior space of the coolant module.

2. The cutting device of claim 1, wherein the coolant comprises a fluid or gas.

3. The cutting device of claim 1, wherein the coolant module is attached to the working blade body and configured to source the coolant to the channels.

4. The cutting device of claim 3, further comprising a main body attached to the working blade body and the coolant module, wherein the main body defines another channel, and
wherein the other channel of the main body is fluidly connected to the channel of the working blade body for provision of coolant stored in the coolant module to the working blade body.

5. The cutting device of claim 1, wherein at least one of the channels is partially a loop shape defined within the working blade body and positioned for delivering the coolant to the second end and for returning coolant from the second end.

6. The cutting device of claim 1, wherein the second end includes a blade edge.

7. The cutting device of claim 1, wherein the second end includes a drill.

8. The cutting device of claim 1, further comprising an inlet attached to the working blade body and defining a pivot point for rotational movement of the working blade body, wherein the inlet is fluidly connected to at least one of the channels for movement of fluid or gas through the inlet and into the at least one of the channels.

9. A cutting device comprising:
a working blade body including a first end and a second end, the first end being configured to operatively connect to a source of movement;
a channel defined within the working blade body for carrying coolant for transferring heat from the second end of the working blade body;
a coolant module attached to the working blade body and configured to source the coolant to the channel, and wherein the coolant module defines an interior space; and
a plurality of cooling fins being positioned within the interior space and positioned to contact coolant within the interior space for transfer of thermal energy from the coolant within the interior space into the cooling fins.

10. A cutting device comprising:
a working blade body including a first end and a second end, the first end being configured to operatively connect to a source of movement; and
a channel defined within the working blade body for carrying coolant for transferring heat from the second end of the working blade body,
wherein the channel is a looping channel comprising a first end and a second end, and
wherein the cutting device further comprises an inlet/outlet attached to the working blade body and defining a pivot point for rotational movement of the working blade body, wherein the inlet/outlet each defines an inlet opening and an outlet opening that fluidly connects to the channel to the first end and the second end of the looping channel for movement of fluid or gas between the inlet opening and the outlet opening.

11. A method comprising:
providing a working blade body including a first end and a second end;
moving the working blade body such that thermal energy is generated within the working blade body; and
using a channel defined within the working blade body for carrying coolant for transferring heat away from the working blade body, wherein the channel is partially a loop shape defined within the working blade body and positioned for delivering the coolant to the second end and for returning coolant from the second end.

12. The method of claim 11, wherein the coolant comprises a fluid or gas.

13. The method of claim 11, further comprising providing a coolant module attached to the working blade body and configured to source the coolant to the channel.

14. The method of claim 13, wherein the coolant module is attached to a main body and defines an interior space for storing the coolant.

15. The method of claim 11, wherein the second end includes a blade edge.

16. The method of claim 11, wherein the second end includes a drill.

17. A method comprising:
providing a working blade body including a first end and a second end;
moving the working blade body such that thermal energy is generated within the working blade body;
using a plurality of channels defined within the working blade body for carrying coolant within the working blade body for transferring heat away from the working blade body; and
storing the coolant in a coolant module, wherein the coolant module is attached to a main body and defines an interior space for storing the coolant, wherein a portion of the main body extends through the interior space of the coolant module.

18. A method comprising:
providing a working blade body including a first end and a second end;
moving the working blade body such that thermal energy is generated within the working blade body;
using a channel defined within the working blade body for carrying coolant for transferring heat away from the working blade body;
providing a coolant module attached to the working blade body and configured to source the coolant to the channel, and wherein the coolant module defines an interior space; and
providing a plurality of cooling fins being positioned within the interior space and positioned to contact coolant within the interior space for transfer of thermal energy from the coolant within the interior space into the cooling fins.

19. A method comprising:
providing a working blade body including a first end and a second end;
moving the working blade body such that thermal energy is generated within the working blade body;
using a channel defined within the working blade body for carrying coolant for transferring heat away from the working blade body, wherein the channel is a looping channel comprising a first end and a second end; and
providing an inlet/outlet attached to the working blade body and defining a pivot point for rotational movement of the working blade body, wherein the inlet/outlet each defines an inlet opening and an outlet opening that fluidly connects to the channel to the first end and the second end of the looping channel for movement of fluid or gas between the inlet opening and the outlet opening.

\* \* \* \* \*